(12) United States Patent
Fukawa et al.

(10) Patent No.: US 11,432,537 B2
(45) Date of Patent: Sep. 6, 2022

(54) METHOD FOR PRODUCING BLOOD CHIMERIC ANIMAL (71) Applicants: National Federation of Agricultural Cooperative Associations, Tokyo (JP); The University of Tokyo, Tokyo (JP)

(72) Inventors: Kazuo Fukawa, Kato-gun (JP); Tetsuya Ito, Kato-gun (JP); Mai Kamikawa, Kato-gun (JP); Yutaka Sendai, Tsukuba (JP); Hiromitsu Nakauchi, Tokyo (JP); Satoshi Yamazaki, Tokyo (JP); Motoo Watanabe, Tokyo (JP)

(73) Assignees: THE UNIVERSITY OF TOKYO, Tokyo (JP); NATIONAL FEDERATION OF AGRICULTURAL COOPERTIVE ASSOCIATIONS, Tokyo (JP)

( * ) Notice: Subject to any disclaimer, the term of this patent is extended or adjusted under 35 U.S.C. 154(b) by 225 days.

(21) Appl. No.: 15/739,059

(22) PCT Filed: Jun. 20, 2016

(86) PCT No.: PCT/JP2016/068233
§ 371 (c)(1),
(2) Date: Dec. 21, 2017

(87) PCT Pub. No.: WO2016/208532
PCT Pub. Date: Dec. 29, 2016

(65) Prior Publication Data
US 2018/0177164 A1    Jun. 28, 2018

(30) Foreign Application Priority Data
Jun. 22, 2015  (JP) .............................. JP2015-124569

(51) Int. Cl.
*A01K 67/027*    (2006.01)
*C12N 15/09*    (2006.01)
*C12N 5/0789*    (2010.01)

(52) U.S. Cl.
CPC ........ *A01K 67/0271* (2013.01); *A01K 67/027* (2013.01); *C12N 5/0647* (2013.01); *C12N 15/09* (2013.01); *A01K 2207/12* (2013.01); *A01K 2217/052* (2013.01); *A01K 2227/108* (2013.01); *A01K 2267/025* (2013.01); *C12N 2510/00* (2013.01); *C12N 2510/02* (2013.01); *C12N 2517/02* (2013.01)

(58) Field of Classification Search
None
See application file for complete search history.

(56) References Cited

U.S. PATENT DOCUMENTS

2007/0124826 A1   5/2007  Hanazono et al.
2012/0251528 A1*  10/2012 Leskov ...................... 424/133.1

FOREIGN PATENT DOCUMENTS

| CN | 102286427 A | 12/2011 | |
|---|---|---|---|
| EP | 1 661 984 A1 | 5/2006 | |
| JP | 2005-229802 A | 9/2005 | |
| JP | 2007-89432 A | 4/2007 | |
| WO | WO 01/58255 A1 | 8/2001 | |
| WO | WO-0158255 A1 * | 8/2001 | ......... A01K 67/0271 |
| WO | WO 2005/019441 A1 | 3/2005 | |
| WO | WO 2011/071085 A1 | 6/2011 | |
| WO | WO 2013/019587 A2 | 2/2013 | |

OTHER PUBLICATIONS

Takaki et al. Enhanced Hematopoiesis by Hematopoietic Progenitor Cells Lacking Intracellular Adaptor Protein, Lnk. Journal of Experimental Medicine, 2002. 195(2):151-160.*
Abe et al., "Ex vivo expansion of human HSCs with Sendai virus vector expressing HoxB4 assessed by sheep in utero transplantation," Experimental Hematology (2011), vol. 39, pp. 47-54.
English translation of International Search Report dated Sep. 13, 2016, in PCT International Application No. PCT/JP2016/068233.
Suzuki et al., "Homeostasis of hematopoietic stem cells regulated by the myeloproliferative disease associated-gene product Lnk/Sh2b3 via Bcl-xL," Experimental Hematology (2012), vol. 40, pp. 166-174.
Takizawa et al., "Control of bone marrow reconstitution capacity of hematopoietic stem cells and progenitor cells by transient inhibition of inhibitory adaptor protein Lnk," Proceedings of the Japanese Society for Immunology (2004), vol. 34, p. 66 (1-D-W5-07-P), with English translation.
Takizawa et al., "Enhanced engraftment of hematopoietic stem/progenitor cells by the transient inhibition of an adaptor protein, Lnk," Blood (2006), vol. 107, pp. 2968-2975.
Extended European Search Report, dated Oct. 17, 2018, for European Application No. 16814302.2.

(Continued)

*Primary Examiner* — Christopher M Babic
*Assistant Examiner* — Kimberly A Aron
(74) *Attorney, Agent, or Firm* — Birch, Stewart, Kolasch & Birch, LLP (57) ABSTRACT

The present invention discloses a novel means capable of producing a blood chimeric animal in which a state of retaining blood cells originating in a heterologous animal at a high percentage is sustained for a long period of time. The method for producing a non-human animal that retains blood cells originating in a heterologous animal, according to the present invention, comprises transplanting hematopoietic cells of a heterologous animal into a non-human animal, in which hematopoietic cells the function of a gene that acts on the hematopoietic system is modified, The gene that acts on the hematopoietic system is, for example, Lnk gene, When a medium to large mammal is used as a recipient, the survival rate of hematopoietic cells originating in a heterologous animal is dramatically increased such that blood chimerism of 10% or more can be maintained even in a 16 month old animal.

5 Claims, 4 Drawing Sheets

Specification includes a Sequence Listing.

(56) References Cited

OTHER PUBLICATIONS

Takaki et al., "Enhanced Hematopoiesis by Hermatopoietic Progenitor Cells Lacking Intracellular Adaptor Protein, Lnk", J. Exp. Med. vol. 195, No. 2, Jan. 21, 2002, pp. 151-160 (10 pages).

* cited by examiner

METHOD FOR PRODUCING BLOOD CHIMERIC ANIMAL

TECHNICAL FIELD

The present invention relates to a method for producing a blood-chimeric non-human animal that retains blood cells of a heterologous animal at a high percentage.

BACKGROUND ART

Non-human animals that retain human blood cells at a high percentage are extremely promising as evaluation systems for evaluating the responses to drugs, diseases, virus infections and the like, and are expected to serve as extremely important model animals in the development in the field of medical science and treatment. So far, blood-humanized mice that retain human hematopoietic cells at a high percentage have been produced, by transplanting human hematopoietic stem cells into super-immunodeficient mice. Since it is difficult to carry out a long-term experiment using blood-humanized mice, and there are some differences in anatomical and physiological characteristics between humans and mice, it is desired to produce animals that retain human blood cells at a high percentage, using pigs and non-human primates that have greater similarities with humans. However, attempts to produce non-human primates or medium to large domestic animals that retain human blood cells at a high percentage have not yet been successful.

To produce a human-blood chimeric animal, a method is known which is capable of producing a human-blood chimeric individual by transplanting human hematopoietic stem cells into a non-human animal fetus in an immunotolerant state (Patent Document 1). The above described method is a technique developed by the present inventors, and is capable of producing a blood chimeric individual that retains human blood cells, even when a large animal such as a pig or sheep is used as a recipient. However, the survival rate of the hematopoietic stem cells in the thus produced individual is low, with the level of blood chimerism being several percent or less. A decrease in the survival rate of the hematopoietic stem cells starts after birth, and heterologous blood cells cannot be retained for a long period of time.

Further, there has been reported a method for transplanting, as donor cells, human hematopoietic stem cells in which HOXB4 gene involved in hematopoiesis is overexpressed, into a sheep fetus (Non-Patent Document 1). However, even with this method, the survival rate of the hematopoietic stem cells is less than 10%, and it is unable to sustain a highly blood chimeric state for a long period of time.

On the other hand, Lnk (also referred to as Sh2b3) is an intracellular adaptor protein which is mainly expressed in hematopoietic cells and lymphoid tissue, and is known to have an inhibitory action on the proliferation and the maturation of megakaryocytes, as well as on the amplification and the hematopoietic function of hematopoietic stem cells. A technique is also known, in which the Lnk gene in embryonic stem cells is knocked out or knocked down to facilitate the differentiation of the stem cells into megakaryocytes, thereby increasing the production of platelets (Patent Document 2). However, the survivability of the hematopoietic stem cells in which the Lnk gene is disrupted, in a heterologous animal, is unknown.

PRIOR ART DOCUMENTS

Patent Documents

Patent Document 1: JP 2005-229802 A
Patent Document 2: JP 2007-089432 A

Non-Patent Documents

Non-Patent Document 1: Abe T et al. Ex vivo expansion of human HSCs with Sendai virus vector expressing HoxB4 assessed by sheep in utero transplantation. Exp Hematol. 39(1), 47-54 (2011).

SUMMARY OF THE INVENTION

Problems to be Solved by the Invention

An object of the present invention is to provide a novel means capable of producing a blood chimeric animal in which a state of retaining blood cells originating in a heterologous animal such as a human at a high percentage is sustained for a long period of time, even when a medium to large domestic animal is used as a recipient.

Means for Solving the Problems

The present inventors have intensively studied the conditions for producing a blood chimeric animal by transplanting hematopoietic stem cells into a fetus. As a result, the inventors have discovered that it is possible to markedly improve the survival rate of murine hematopoietic stem cells in pigs, and to obtain blood chimeric pigs in which a high blood chimerism of 10% or more is sustained even at 16 months old, by transplanting into pig fetuses murine hematopoietic stem cells in which Sh2b3/Lnk, which is an intracellular adaptor protein mainly expressed in hematopoietic cells and lymphoid tissue, is deleted, as donor cells. Thus, it has been discovered that the modification of the function of the Lnk gene or another adequate gene that acts on the hematopoietic system, in the donor cells, enables to markedly improve the survival rate of donor hematopoietic cells originating in a heterologous animal, and to produce a non-human animal in which a blood chimeric state is sustained for a prolonged period of time. The present invention has been completed based on the above findings.

That is, the present invention provides a method for producing a non-human animal that retains blood cells originating in a heterologous animal, the method including transplanting hematopoietic cells of a heterologous animal into a non-human animal, wherein the hematopoietic cells are cells in which a function of a gene that acts on the hematopoietic system is modified. Further, the present invention provides a non-human animal that retains blood cells originating in a heterologous animal, in which hematopoietic cells originating in a heterologous animal survive, the hematopoietic cells being cells in which a function of a gene that acts on the hematopoietic system is modified, and which retains blood cells originating in the heterologous animal in the circulating blood. Still further, the present invention provides a method for producing blood cells, the method including collecting blood from the non-human animal according to the present invention as described above, and separating the blood cells originating in the heterologous animal.

Effect of the Invention

The present invention makes it possible to provide a blood-chimeric non-human animal in which a high level of chimerism is sustained for a long period of time. According to the method of the present invention, it is possible to dramatically improve the survival rate of hematopoietic cells originating in a heterologous animal, and to sustain a blood chimerism of 10% or more even after 16 months after birth, in a recipient, even when a medium to large mammal, such as a pig, is used as the recipient. No attempt has ever been successful in producing an animal that stably retains blood cells of a heterologous animal at a high percentage of 10% or more, using a non-human primate or a medium to large domestic mammal as a recipient, and the present invention is the first to allow the production of such an animal. When a normal non-human animal that does not present immunodeficiency is used to produce a blood chimeric animal, a special environment, such as a clean room, is not required, and the animal can be reared under a common rearing environment, while retaining its high level of chimerism. Blood chimeric animals that retain blood of a heterologous animal at a high percentage can be used as models for evaluating drugs, diseases, virus infections and the like, and are useful for screening of drugs. Further, studies have been done on techniques of producing organs for transplantation into humans, in domestic animals, such as pigs. Since domestic animals that retain human blood cells at a high percentage are thought to be immunologically tolerant to human cells, it is considered that such animals are also suitable for producing organs for transplantation into humans, and can be effectively used for preserving human organs. In addition, the production of blood chimeric animals that retain human blood cells at a high percentage, using large animals, allows for mass production of human blood cells, and thus is extremely promising as a technique that provides an alternative for blood donation.

BRIEF DESCRIPTION OF THE DRAWINGS

FIG. 1a shows an example of one-parameter histograms obtained by flow cytometry of the blood samples of murine-blood chimeric pig offsprings, using an anti-mouse CD45 antibody. FIG. 1b shows the results of calculation of the percentage of murine nucleated blood cells with respect to the total nucleated blood cells in each blood sample. FIG. 1c shows an example of two-parameter histograms of granulocytes and B cells detected in the blood samples of murine-blood chimeric pig offsprings. FIG. 1d shows an example of two-parameter histograms of granulocytes and T cells detected in the blood samples of murine-blood chimeric pig offsprings.

MODE FOR CARRYING OUT THE INVENTION

In the method for producing a blood-chimeric non-human animal according to the present invention, hematopoietic cells in which the function of a gene that acts on the hematopoietic system is modified are transplanted into a non-human animal. The hematopoietic cells are hematopoietic cells of a heterologous animal that is different from the non-human animal to be used as a recipient, and may be hematopoietic stem cells or hematopoietic progenitor cells. In general, the hematopoietic cells are a cell population comprising hematopoietic stem cells.

The non-human animal is preferably a medium to large mammal, and may be, for example, a medium to large domestic mammal. Specific examples of the medium to large mammal include: various types of ungulate animals, including even-toed ungulates such as pigs, cattle, goats, sheep, deer and camels, and odd-toed ungulates such as horses; as well as monkeys; but not limited thereto. The domestic animal may typically be an ungulate animal. In the case of making a non-primate produce human blood, a pig is particularly preferably used, in view of its anatomical similarities with a human, and the like.

The heterologous animal is not particularly limited, as long as it is an animal of a species different from the non-human animal to be transplanted with the hematopoietic cells. However, the heterologous animal is typically a mammal, and most preferably a human.

The modification of gene function is inhibition or facilitation of the gene function. In general, in cases where a gene to be modified has an inhibitory action on the hematopoietic system, the modification can be achieved by inhibiting the function of the gene; whereas in cases where a gene to be modified has a facilitatory action on the hematopoietic system, the modification can be achieved by facilitating the function of the gene.

The expression "to inhibit the function of a gene" refers to causing a decrease in or loss of the production or the accumulation of an mRNA or a protein that is originally encoded by the gene, for example, by modifying at least a part of the region of the gene on the genome, in the hematopoietic cells to be used in the transplantation; and the expression includes from a decrease in the function of the gene, to a complete loss of the function. Gene modification methods for inhibiting the function of a particular gene are widely known in the art, and those skilled in the art will be able to select an appropriate method to carry out the modification. The methods are largely classified into two categories: gene disruption methods (knock out methods) whereby the function of a gene is deleted; and gene knock down methods whereby the function of a gene is decreased. Specific examples of the knock out method include: a knock out method by homologous recombination using a targeting vector; a zinc finger nuclease (ZFN) method (Porteus, M. H. et al. Gene targeting using zinc finger nucleases. Nat. Biotechnol. 23, 967-973 (2005).); a TALEN method (Christian, M. et al. Targeting DNA double-strand breaks with TAL effector nucleases. Genetics 186, 757-761 (2010).); and a CRISPR/Cas9 method (Sander, J. D. et al. CRISPR-Cas systems for editing, regulating and targeting genomes. Nat Biotechnol 32, 347-355 (2014).). Specific examples of the knock down method include an antisense method, and an RNAi. A highly efficient knock down of a gene allows for obtaining a result equivalent to that obtained by knocking out the gene. Further, it is also possible to inhibit the function of a gene, by introducing a dominant negative mutation.

The expression "to facilitate the function of a gene" refers to causing an increase in the amount of production or accumulation of an mRNA or a protein encoded by the gene, in the hematopoietic cells to be used in the transplantation. The facilitation of the function of a gene can be achieved, for example, by overexpressing the gene.

The hematopoietic cells in which the function of a gene that acts on the hematopoietic system is modified can be obtained from bone marrow cells or umbilical cord blood of an animal in which the function of the gene is modified in the manner as described above. Or, hematopoietic cells may be collected from bone marrow cells or umbilical cord blood of an animal that does not have such a genetic modification, and the function of a desired gene in the collected cells may then be modified. Furthermore, it is also possible to prepare hematopoietic cells in which the function of a gene that acts on the hematopoietic system is modified, by modifying the function of the desired gene in cells having a pluripotency (hereinafter, referred to as pluripotent cells) such as embryonic stem cells (ES cells) and induced pluripotent stem cells (iPS cells), and then inducing the modified cells to differentiate into hematopoietic cells. In cases where pluripotent cells are induced to differentiate into hematopoietic stem cells, the resulting cell population may comprise hematopoietic progenitor cells in addition to the hematopoietic stem cells. Such a cell population can be used as the hematopoietic cells to be transplanted into a non-human animal.

Specific examples of the pluripotent cells which can be used when hematopoietic cells are differentiated from pluripotent cells include the above described embryonic stem cells (ES cells), induced pluripotent cells (iPS cells), as well as embryonic carcinoma cells (EC cells), embryonic germ cells (EG cells), and multipotent germ cells (mGS cells).

As a specific preferred example of a gene that acts on the hematopoietic system, Lnk gene (also referred to as Sh2b3 gene) can be mentioned, as a first choice. The Lnk gene is known to have an inhibitory action on the proliferation and the maturation of megakaryocytes, as well as on the amplification and the hematopoietic function of hematopoietic stem cells. Accordingly, in cases where the Lnk gene is a target gene to be modified, the modification can be achieved by preparing hematopoietic cells in which the function of the Lnk gene is inhibited.

For example, human hematopoietic cells in which the function of the Lnk gene is inhibited can be prepared by carrying out a genetic modification to inhibit the function of the Lnk gene in a human pluripotent cell strain, and inducing differentiation of the resulting cell strain with inhibited Lnk gene function into hematopoietic cells. In this case, human iPS cells can be preferably used, from an ethical standpoint that it allows for preparing the hematopoietic cells without destroying human embryos. iPS cells, as well known in the art, are cells having a pluripotency similar to that of ES cells, and prepared by introducing cell reprogramming factors into somatic cells of an animal individual. The methods for preparing iPS cells from somatic cells are well known.

The Lnk gene has been identified in various species of animals, including humans, and is well known. Human Lnk gene is located on chromosome 12 (12q24, Annotation release 107, GRCh38.p2 (GCF_000001405.28), NC_000012.12 (111405108 . . . 111451624)), and information about its sequence and the like has been deposited under Gene ID: 10019, Accession No. NM_005475, in the NCBI database. The sequences shown in SEQ ID NOs: 1 and 2 in Sequence Listing are the cDNA sequence of the human Lnk gene and the amino acid sequence encoded thereby which are deposited under NM_005475. Human Lnk protein has the dimer-forming domain at aa1-193, the pleckstrin homology (PH) domain at aa206-307, and the Src homology 2 (SH2) domain at aa364-462.

Examples of the method for inhibiting the function of the Lnk gene in a human pluripotent cell strain include knockout of the Lnk gene, RNAi using siRNA against the Lnk gene, and introduction of a dominant negative mutation.

The knockout of the Lnk gene can be carried out, for example, by deleting the coding region or promoter region of the Lnk gene in both alleles in the genome of pluripotent cells, or by inserting a stop codon or introducing a mutation such as substitution or insertion of an amino acid so as to disable the production of a normal Lnk protein. In the case of deleting the coding region, the entire coding region may be deleted, or part thereof may be deleted. A homozygous Lnk KO mouse used in the following Examples is a mouse in which exons 2 to 7 in the coding region of the Lnk gene are deleted. It is thought that the Lnk gene in human cells can also be knocked out, by deleting the corresponding region. Further, all or part of the coding region of the Lnk gene may be replaced by a sequence of a marker gene for drug resistance, a fluorescent protein, or the like, for the sake of convenience in the screening of a knockout cell line.

The knockout method using a targeting vector can be carried out by: amplifying the genomic sequences on the upstream and the downstream sides of a desired region to be deleted, from the genomic DNA of a heterologous animal, using PCR, to prepare an upstream homology region and a downstream homology region; inserting these homology regions and a marker gene one by one into an appropriate plasmid vector, to construct a targeting vector containing a DNA construct for gene disruption, in which construct the upstream homology region, the marker gene, and the downstream homology region are arranged in the order mentioned; and introducing the resulting targeting vector into pluripotent cells of the heterologous animal by a conventional method such as electroporation. When such a targeting vector is introduced into cells, the construct for gene disruption is introduced into an intended position on the genome through homologous recombination, to generate a mutant allele in which all or part of the Lnk gene is replaced by the marker gene.

The size of the upstream homology region and the downstream homology region affects the efficiency of the homologous recombination, and thus, homology regions having a larger size are used for a biological species with lower recombination efficiency. In gene disruption in mammals, homology regions of about several kilobases in size are commonly used. In general, a homology region with a size of about 1 to 3 kb (short arm) is used for one of the homology regions, and one with a size of about 5 kb or more (long arm) is used as the other homology region. However, both the homology regions may be prepared to have a size of about 5 kb. Since the sequence information of the entire genome (such as BAC sequence, shotgun sequence and the like) has been identified in various species of animals including humans and deposited in databases, sequence information necessary for the preparation of the homology regions is available from such databases.

In mammalian cells, the frequency of introduction of a construct for gene disruption into a genome through homologous recombination is very low, as compared to the frequency of random introduction not through homologous recombination. Therefore, in the case of knocking out the Lnk gene in pluripotent cells of a mammal such as a human, it is preferred to use a positive selection marker that confers drug resistance and a negative selection marker that confers drug sensitivity in combination. When using these markers in combination, in the above described construct for gene disruption, the positive selection marker gene can be used as a marker gene that is incorporated between the two homology regions, and the negative selection marker gene can be arranged outside of the two homology regions (i.e. on the 5' side of the upstream homology region, or on the 3' side of the downstream homology region). With this arrangement, if the construct is introduced into the genome through homologous recombination, a region of the construct outside the homology region is not introduced into the genome, and thus the drug sensitivity is not conferred to the transformed cells by the negative selection marker gene. On the other hand, if the construct is introduced into the genome through a mechanism other than homologous recombination, the negative selection marker gene is also introduced into the genome, and thus the drug sensitivity is conferred to the thus transformed cells. Therefore, if such a construct for gene disruption is introduced into pluripotent cells and thereafter the screening of cells is carried out using the positive selection marker and the negative selection marker, pluripotent cells in which the construct is introduced at an appropriate position through homologous recombination and the Lnk gene is disrupted can be efficiently selected.

Specific examples of commonly used marker genes include: neomycin-resistant gene, blasticidin-resistant gene and puromycin-resistant gene, which are used as a positive selection marker; and thymidine kinase gene and diphtheria toxin A fragment (DT-A), which are used as a negative selection marker; but not limited thereto. Each of these markers is used in combination with an appropriate promoter, and those skilled in the art can appropriately select it, depending on the type of marker genes.

After the screening with these markers, the disruption of the gene is confirmed by PCR or Southern blotting, and cells having an allele in which the Lnk gene is disrupted are obtained. Those skilled in the art can design, as appropriate, primers used for PCR and a probe used for Southern blotting depending on the structure of DNA construct for gene disruption.

Since the frequency of homologous recombination is very low in mammalian cells, as described above, it is highly unlikely that homologous recombination takes place in both alleles at the same time, and thus the resulting cells are usually heterozygous knockout cells. Homozygous knockout cells can be obtained by repeating the above described introduction of the construct for gene disruption and screening of cells, using a cell line which has been confirmed to be a heterozygous knockout cell line. Homozygous knockout cells can be properly selected by using a DNA construct for gene disruption comprising a drug-resistant positive selection marker in preparation of heterozygous knockout cells and using a DNA construct for gene disruption comprising another drug-resistant positive selection marker, which is different from the former, in preparation of homozygous knockout cells.

In order to improve the efficiency of homologous recombination, BML gene knockdown treatment may be carried out, in addition to the Lnk gene knockout treatment. It has been reported that BML gene knockdown treatment improves the efficiency of homologous recombination in human cells (So S et al. Genes to Cells 2006; 11(4):363-371.), and thus the knockdown of the BML gene is thought to be similarly effective in improving the efficiency of homologous recombination in humans and in animals other than humans. Sequence information and the like of the BML gene are also known, and nucleic acid reagents for knocking down the BML gene in various animal species are commercially available. Thus, those skilled in the art can carry out the BML gene knockdown treatment, using as appropriate any of such commercially available products.

A method for knocking down a target gene by RNAi is also well known, which is an established technique. A cell line in which the Lnk gene is constitutively knocked down by RNAi can be obtained by allowing siRNA to be produced in cells using an expression vector such as a plasmid vector or a virus vector. In general, a method is used in which a vector that expresses a hairpin RNA (shRNA) is prepared, and the thus prepared vector is introduced into cells to induce RNAi in the cells. The shRNA expressed in a cell is recognized and cleaved by Dicer to generate siRNA. siRNA and shRNA against the Lnk gene can also be designed based on the sequence information of the Lnk gene. Various types of expression vectors are known for producing siRNA in cells. Further, there are many service providers that provide commissioned services such as siRNA/shRNA designing, preparation of an expression vector for RNAi, preparation of a knockdown cell line by RNAi, and the like, and such service providers may also be used.

One example of the literatures which disclose actual examples of the knockout and knockdown of the Lnk gene in human pluripotent cells is a literature written by Felix C. Giani, et al., "Targeted Application of Human Genetic Variation Can Improve Red Blood Cell Production from Stem Cells", Cell Stem Cell 18, 73-78, Jan. 7, 2016. Giani et al. have performed a knockout of the Lnk gene by a CRISPR/Cas9 method, and a knockdown by RNAi, targeting a region within exon 3 of the Lnk gene (a region in the SH domain). Specifically, in the knockout by the CRISPR/Cas9 method, CGG encoding the $261^{th}$ arginine is used as a PAM (protospacer adjacent motif), and a guide RNA targeting the 20 bases directly flanking before the PAM (the region from the $1118^{th}$ to $1137^{th}$ position in the sequence of SEQ ID NO: 1) is designed, so that a DNA double-strand break is induced within the exon 3 (in the SH domain) to cause a frame shift, thereby knocking out the Lnk gene. It has been also confirmed that, when human pluripotent cells in which the Lnk gene is knocked out are allowed to differentiate into hematopoietic cells, the production of erythrocytes is markedly increased. In the knockdown by RNAi, an shRNA is also designed to target the region within exon 3 (region in the SH domain). The sequences of shRNA constructs used by Giani et al. are shown in SEQ ID NOs: 3 and 4. It has been confirmed that erythroid differentiation is facilitated when a lentivirus vector is used to express shRNA in hematopoietic stem cells and hematopoietic progenitor cells to knock down the Lnk gene. The method performed by Giani et al. can also be preferably used in the present invention to prepare human hematopoietic cells in which the Lnk gene is knocked out or knocked down.

Further, the above described literature by Giani et al. discloses the followings, as natural missense mutations capable of causing a loss or marked impairment of the function of the Lnk gene: E208Q, S213R, I257R, E301K, S370C, S394G, E395K, E400K, R425C, I446V, and R518*. The inhibition of the function of the Lnk gene can also be achieved by introducing any of these mutations into both alleles of the Lnk.

Dominant negative mutations of Lnk are also known. For example, JP 2007-89432 A discloses a dominant negative mutant of murine Lnk, which is considered to be also usable as a dominant negative mutant in human Lnk. Specific examples of the dominant negative mutant of Lnk include mutations in the SH2 domain (such as a substitution mutation of the $364^{th}$ arginine to glutamic acid), deletion mutations of the PH domain, deletion mutations of the C-terminal domain, and combinations of these mutations. In the amino acid sequence of human Lnk shown in SEQ ID NO: 2, the PH domain is the region from the 194$^{th}$ to 309$^{th}$ amino acids; the SH2 domain is the region from the 355$^{th}$ to 451$^{th}$ amino acids; and the C-terminal domain is the region from the 452$^{th}$ to 575$^{th}$ amino acids in which the tyrosine phosphorylation domain is located. The region of the dominant negative C-terminal deletion mutation known in mice corresponds to the region from the 526$^{th}$ to 575$^{th}$ amino acids in human Lnk. By introducing such a dominant negative mutant into pluripotent cells, the function of the Lnk gene on the genome can be inhibited. Introduction of a dominant negative mutant into cells can be carried out, for example, using a virus vector or the like.

Although the knockout and knockdown operations have been described hereinabove with reference to the Lnk gene as a primary example, it is also possible to carry out the knockout and knockdown of other genes that act on the hematopoietic system in the same manner.

In some cases, due to a gene modification operation such as knockout or knockdown operation, a marker gene is introduced on the genome of hematopoietic cells, and in such cases, the marker gene is also present on the genome of nucleated blood cells among the blood cells differentiated from such hematopoietic cells. If the presence of the marker gene is not desired, a gene modification method which does not cause the marker gene to remain on the genome (such as a method using TALEN or CRISPR/Cas9, or knock down by RNAi) can be used to carry out the functional modification of a gene that acts on the hematopoietic system, such as the Lnk gene. Or, it is also possible to remove the marker gene present in the genome using a loxP/Cre recombinant system. For example, in cases where hematopoietic cells in which Lnk is knocked out are transplanted into a non-human animal to make the animal produce human blood, a marker gene into which a loxP sequence is inserted at each of the 3' and 5' ends thereof in advance is used to construct a knockout vector, and the resulting vector is used to produce a Lnk-knockout strain of human pluripotent cells. Then the marker gene region sandwiched by the loxP sequences can be removed from the genome of the Lnk-knockout cells, by infecting the thus prepared Lnk-knockout strain, or the Lnk-knockout hematopoietic cells that have been differentiated from the strain, with an adenovirus or the like that expresses a Cre recombinase.

As a method for inducing differentiation of hematopoietic cells from pluripotent cells, a method is known, for example, in which the differentiation is induced via teratoma formation (WO 2011/071085).

In this method, pluripotent cells are transplanted subcutaneously in, or into the testes, bone marrow or the like of, a non-human mammal, so as to induce teratoma formation in the body of the non-human mammal. At this time, cocultured cells may be transplanted together with the pluripotent cells, in order to improve the efficiency in inducing differentiation. Examples of the cocultured cells include feeder cells and stromal cells, of which OP-9 cells can be preferably used, for example. In the case of transplanting human iPS cells into a mouse, the improvement can be achieved by transplanting iPS cells in a number of about 1 to 10×10$^6$ and cocultured cells in an amount of about 1/10 to 1/2 of that of the iPS cells.

A differentiation inducer such as stem cell factor (SCF), thrombopoietin (TPO) or the like is administered to the non-human mammal that has been transplanted with the cells. In general, the differentiation inducer is continuously administered subcutaneously, for example, using an osmotic pump.

The non-human mammal after the transplantation is reared for an adequate period of time, until a teratoma having a sufficient size is formed therein. In general, a teratoma having a sufficient size is formed within about 4 to 12 weeks after the transplantation. From the thus obtained teratoma, hematopoietic cells such as hematopoietic stem cells and the like can be separated. Further, since the differentiated hematopoietic cells migrate from the teratoma to survive also in the bone marrow, hematopoietic cells of interest can also be collected from the bone marrow. For example, in the case of separating and collecting human hematopoietic stem cells from teratoma tissue or bone marrow cells, the human hematopoietic stem cells can be specifically sorted out and collected by a magnetic cell separation method or a cell sorting method, using an anti-human CD34 antibody, an anti-human CD117 antibody, or an anti-human 133 antibody or the like, which is an antibody against a surface antigen of human hematopoietic stem cells. However, the above described method for sorting and collecting hematopoietic cells is a mere example, and any other method may be used.

In the manner as described above, human iPS cells can be induced to differentiate into hematopoietic cells such as hematopoietic stem cells and the like within the body of an experimental animal such as a mouse, to obtain a hematopoietic cell population for transplantation used in the present invention. However, the above described differentiation induction method via teratoma formation is a mere example of the method for inducing pluripotent cells to differentiate into hematopoietic cells, and any other method may be used.

The transplantation of hematopoietic cells may be carried out on a fetus of a non-human animal, or on a postnatal non-human animal individual. In the case of transplantation into a postnatal individual, a common bone marrow transplant method may be used. In the case of transplantation into a non-human animal individual that presents a symptom of immunodeficiency, the administration of an immunosuppressant can be omitted. The cell transplantation into a fetus can be carried out by in utero transplantation. The in utero transplantation may be carried out after performing an abdominal section on a mother animal, or may be carried out transdermally without performing an abdominal section. Methods for carrying out the in utero transplantation as described above are well known, and specific procedures thereof are disclosed, for example, in JP 2005-229802 A and the like.

In an in utero transplantation method, a pregnant non-human animal is subjected to general anesthesia, shaved, and then thoroughly washed and disinfected. The transplantation of hematopoietic cells is then carried out, while observing the fetus in the uterus from the surface of the skin or the uterus with an ultrasonic tomographic equipment. The cell transplantation is carried out using an injection needle or a puncture needle. The size of the needle to be used varies depending on the species of the non-human animal, and a needle having a size of about 22 to 27 gauges is usually used in the case of transplantation into a medium to large mammal.

In cases where transplantation is performed on a non-human animal fetus whose function of the immune system is deficient, the age in days of the fetus at the time of transplantation is not particularly limited. In the case of using a normal non-human animal that does not present a symptom of immunodeficiency, the transplantation into a fetus needs to be performed during the period when the fetus is in an immunotolerant state. In pigs, immunotolerance starts to decline after about 50 days old. Therefore, in the case of using a pig as a recipient, the transplantation is preferably carried out to a pig fetus of about 60 days old or less, such as, for example, 20 to 60 days old, 20 to 55 days old, 30 to 55 days old, 30 to 52 days old, or 30 to 50 days old. The age in days of a fetus as used herein refers to a fetal age, which is the age expressed in days, taking the day of fertilization or the day of mating as 0 days old. A strain that presents a symptom of immunodeficiency is also known in pigs (see, e.g. JP 2015-002719 A), and in the case of transplanting the cells into such an immunodeficient pig fetus, a fetus at a fetal age higher than the above described range can also be used as a recipient for the cell transplantation.

The site into which the hematopoietic cells are transplanted is not particularly limited. In general, a high survival rate of the donor cells can be achieved by transplanting the cells into the heart of a fetus. Due to the recent improvements in the performance of ultrasonographic diagnostic apparatuses, it has become possible to transplant cells while confirming the position of the heart even in a fetus at several tens of days of age or younger. Note, however, that the cells may also be transplanted into another organ such as liver, or into another site such as within the abdominal cavity. After the cell transplantation, an antibiotic is injected into the abdominal cavity or amniotic cavity of the fetus, as necessary. It is preferred to administer an antibiotic also to the mother animal after the transplant operation, for the purpose of preventing infections.

In the case of using an animal that gives multiple births, such as a pig, cell transplantation is usually performed to only some of the fetuses in the uterus (such as, about 2 to 5 fetuses). A short metal wire or the like may be inserted into an appropriate site in the abdominal cavity or the like of each of the recipient fetuses, as a marker identifiable by X-ray, so that the transplanted fetuses can be easily distinguished from the non-transplanted fetuses at delivery.

The fetus(es) transplanted with the cells is/are allowed to grow in the body of the mother animal, to be delivered naturally or by Cesarean section. In this manner, it is possible to obtain a blood chimeric non-human animal individual(s) that retain(s) blood cells originating in a heterologous animal. A non-human animal obtained as described above has a blood chimerism of 10% or more, for example, the animal may have a blood chimerism of 11% or more, 12% or more, 13% or more, 14% or more, or 15% or more. According to the method of the present invention, it is even possible to produce a non-human animal individual having a blood chimerism of 20% or more. A blood chimeric animal obtained by the method according to the present invention is capable of sustaining a high level of blood chimerism, as described above, for a long period of time. For example, in a blood chimeric animal according to the present invention, a high level of blood chimerism as described above is sustained at a time point 3 months, 6 months, 10 months, or 12 months after the transplantation of the hematopoietic cells. In cases where the blood chimeric animal is produced by transplanting hematopoietic cells into a fetus of a non-human animal, a high level of blood chimerism as described above is sustained in the resulting offspring at the age of 3 months old, 6 months old, 10 months old, or 12 months old.

The term "blood chimerism" as used in the present invention refers to the percentage of the blood cells originating in a heterologous animal with respect to the total blood cells present in the circulating blood. The blood cells include erythrocytes, leukocytes and platelets. The leukocytes include granulocytes (neutrophils, eosinophils and basophils), lymphocytes and monocytes. The nucleated blood cells include leukocytes, erythroblasts, megakaryocytes, hematopoietic stem cells and hematopoietic progenitor cells. The nucleated blood cells present in the circulating blood are primarily leukocytes. Although erythroblasts, megakaryocytes, hematopoietic stem cells and hematopoietic progenitor cells are also present in the circulating blood, the amounts thereof are minute. Therefore, the term "blood chimerism" as used in the present invention includes the chimerism of leukocytes (nucleated blood cells), the chimerism of erythrocytes, and the chimerism of platelets.

The blood chimerism can be easily analyzed by a flow cytometric analysis of peripheral blood. Specific examples of typical surface markers include: CD45 for leukocytes, TER-119 for erythrocytes, CD41 for platelets, and Gr-1 for granulocytes. The flow cytometric analysis of a peripheral blood sample can be carried out, using a labeled antibody against any of these markers.

Blood chimeric animals that retain blood of a heterologous animal at a high percentage can be used as models for evaluating drugs, diseases, virus infections and the like, and are useful for screening of drugs. Further, studies have been done on techniques of producing organs for transplantation into humans, in domestic animals, such as pigs. Pigs that retain human blood at a high percentage can be suitably used for producing organs for transplantation into humans.

In addition, the production of blood chimeric animals that retain human blood cells at a high percentage, using large animals, allows for mass production of human blood cells, and thus is promising as a technique that provides an alternative for blood donation. The blood of a blood chimeric animal also contains blood cells originally present in the animal. However, it is possible to separate and collect the blood cells of interest that are originating in a heterologous animal, for example, by: collecting blood from the blood chimeric animal, and carrying out sorting of blood cells, using an antibody against a surface antigen specific to the blood cells of interest that are originating in the heterologous animal (for example, an antibody against human TER-119, in the case of collecting human erythrocytes produced in a pig). When it is desired to further increase the retained amount of erythrocytes and platelets originating in the heterologous animal, it can be achieved, for example, by administering a cytokine such as erythropoietin, thrombopoietin or the like to the blood chimeric animal, to facilitate the production of erythrocytes and platelets from the hematopoietic stem cells originating in the heterologous animal, that survive in the bone marrow.

EXAMPLES

The present invention will now be described specifically, with reference to Examples. However, the present invention is in no way limited by the following Examples.

1. Preparation of Murine Hematopoietic Stem Cells in which Lnk Gene is Knocked out As a homozygous Lnk knockout mouse, a known mouse strain (Takaki et al., 2000. Control of B cell production by the adaptor protein lnk. Definition of a conserved family of signal-modulating proteins. Immunity. 13:599-609.; JP 2007-89432 A) which has been maintained in the animal experimental facility of The Institute of Medical Science of The University of Tokyo, under special pathogen-free conditions, was used. This mouse strain was produced by: producing heterozygous Lnk knockout mice from murine ES cells in which the coding region of the Lnk gene was disrupted by a targeting vector; and by mating the thus produced heterozygous Lnk knockout mice with each other.

Hematopoietic stem cells to be used in the transplantation into pig fetuses were obtained as a cell population enriched with hematopoietic stem cells by collecting bone marrow from the homozygous Lnk knockout mouse, separating nucleated cells by specific gravity centrifugation, and then carrying out magnetic cell separation or cell sorting.

2. Transplantation of Hematopoietic Stem Cells to Pig Fetuses

The hematopoietic stem cells originating in the homozygous Lnk KO mouse were transplanted into the livers of pig fetuses under ultrasonic guide by in utero transplantation, in accordance with the method described in JP 2005-229802 A. Pig fetuses of a crossbred of Duroc species and Large White species (day of mating: Apr. 1, 2013; day of in utero transplantation: May 10, 2013; fetal age: 39 days old), which had been impregnated by artificial insemination, were used to be transplanted with the hematopoietic stem cells. Breeding and rearing management of pigs were carried out in an SPF environment.

(1) Anaesthesia

On the day of transplantation, a pregnant pig was preanaesthetized by an intramuscular injection of midazolam, medetomidine, and atropine sulfate, and then inhalation anesthesia was carried out using a mask. Laughing gas, oxygen and isoflurane were used for the inhalation anesthesia.

(2) Disinfection and Abdominal Section

After anesthetizing the pregnant pig, its abdomen was shaved, thoroughly washed with a povidone-iodine preparation, and then thoroughly disinfected with Isodine. The abdomen of the mother pig was opened to expose its uterus.

(3) Visualization of Pig Fetuses by Ultrasound

An ultrasonic tomographic equipment, Aloka ultrasound diagnostic equipment SSD-500 (ALOKA CO., LTD., Tokyo, Japan) was used for the identification of the pig fetuses and the injection of the cells, and the transplantation was carried out through the uterus. A 7.5 MHz electronic linear probe (Aloka; UST-5820-5) was used as an ultrasonic probe.

(4) Puncture Needle

As a puncture needle to be used for introducing the hematopoietic stem cells into each fetus, a 25-gauge injection needle (NIPRO, Osaka, Japan) was used. The positions of organs were confirmed by the ultrasonic image, and the hematopoietic stem cells of the homozygous Lnk KO mouse were injected into the liver of each fetus. The cells were transplanted to some (five fetuses) of the pig fetuses in the uterus.

(5) Injection of Cells

The hematopoietic stem cells in a number of $3.47 \times 10^6$ were suspended in 0.2 mL of phosphate buffered saline, and the resulting suspension was injected to each of the recipient fetuses through the puncture needle. Subsequently, 0.2 ml of an antibiotic was injected into the abdominal cavity of each fetus. The puncture needle was then removed, and the abdomen of the mother pig was closed.

(6) Postoperative Administration of Antibiotic

To the pregnant pig, an antibiotic was administered by an intramuscular injection over two days after the operation.

(7) Delivery

The delivery was done on Jul. 25, 2013, through natural delivery.

3. Analysis of Offsprings (1) Method

Peripheral blood was collected from each of the offsprings at about 1 week old, about 45 days old and about 16 months old, and the chimerism of blood cells was analyzed by flow cytometry. Peripheral blood of a wild type pig was used as a negative control, and peripheral blood of a wild type C57BL/6 mouse was used as a positive control. A non-transplanted offspring which was a littermate of the recipient offsprings was taken as a littermate control.

For the analysis of nucleated blood cells, blood samples from which erythrocytes were removed were used. To each of the collected blood samples, a hemolytic solution was added to remove erythrocytes, and the resultant was washed with phosphate-buffered saline supplemented with fetal bovine serum, and then mixed with an anti-mouse antibody. An antibody reaction was allowed to proceed under shading and refrigerated conditions, and thereafter, phosphate-buffered saline supplemented with fetal bovine serum was added to the resultant to perform washing, and the thus prepared sample was subjected to the flow cytometry analysis.

At 45 days old, a FITC-labeled anti-mouse CD45 antibody was used to detect mature murine leukocytes (all the nucleated blood cells), a PE-labeled anti-mouse Gr-1Mac1 antibody was used to detect mature murine granulocytes, an APC-labeled mouse CD3e antibody was used to detect murine T cells, and an APC-Cy7-labeled mouse B220 antibody was used to detect murine B cells.

At 16 months old, a PE-labeled anti-mouse CD45 antibody was used to detect mature murine leukocytes (all the nucleated blood cells), and a FITC-labeled anti-mouse Gr-1 antibody was used to detect mature murine granulocytes. Further, the number of mouse Gr-1 positive cells was analyzed by gating on mouse CD45 positive cells, to measure the percentage of the murine granulocytes in the murine leukocytes.

(2) Results

Of the five fetuses that had received cell transplantation, one was deceased at about 10 days after birth. Therefore, the analysis on and after 45 days old was performed only for the remaining four offsprings.

Figure 1:
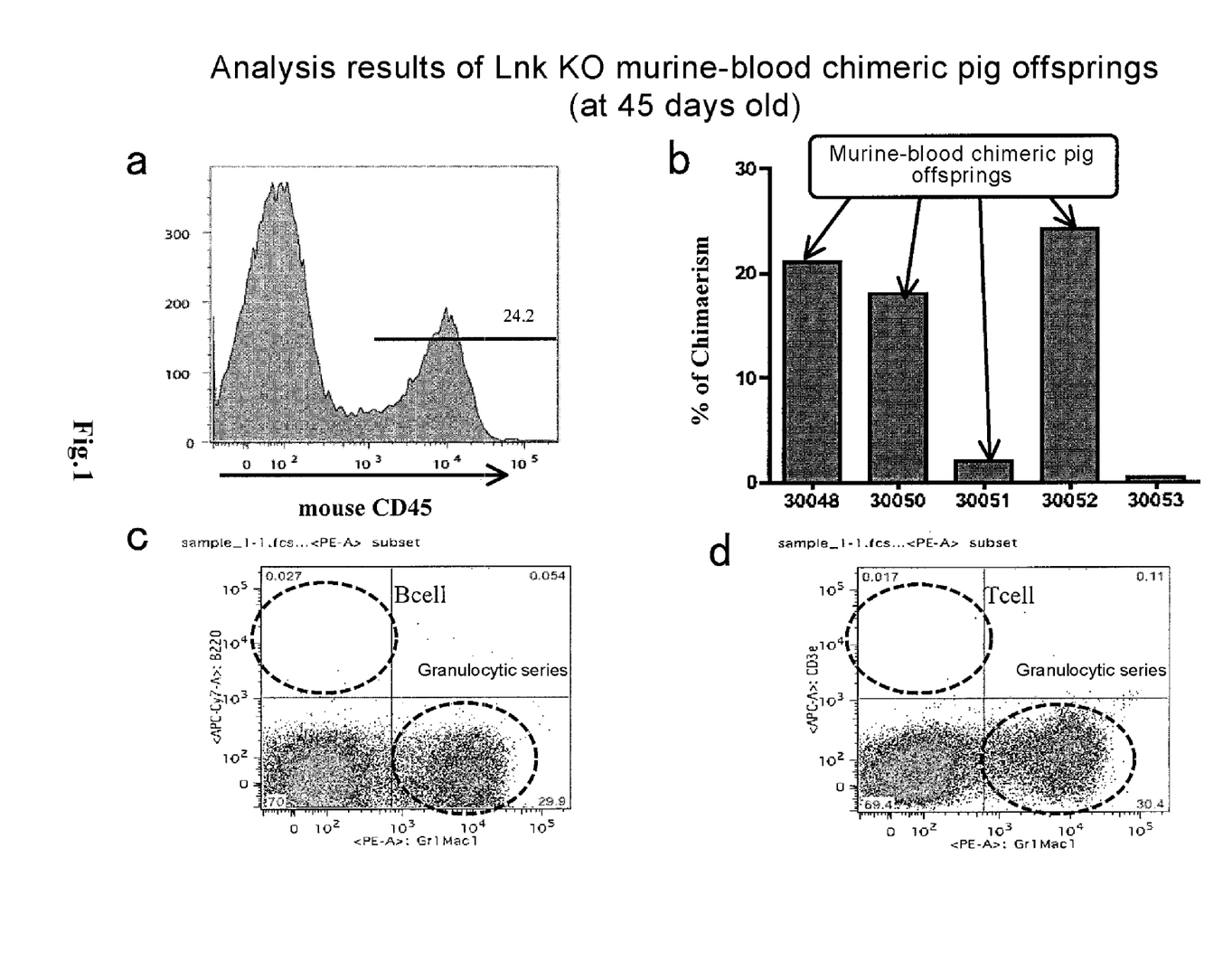
FIG. 1 shows the results of flow cytometric analysis of blood samples collected from pig offsprings produced in Examples at 45 days old.

FIG. 1 shows the results of the analysis for the nucleated blood cells in the blood samples from the obtained pig offsprings at 45 days old. The individual IDs 30048, 30050, 30051 and 30052 represent pig offsprings transplanted with the cells, and the individual ID 30053 represents a non-transplanted littermate. As shown in FIG. 1b, all of the four survived recipient offsprings were blood chimeric pigs that retained murine nucleated blood cells as part of their nucleated blood cells. The three (30048, 30050 and 30052) of the four offsprings each showed a chimerism of greater than 15%. Regarding the trend of differentiation, the granulocytic series accounted for the most of the detected cells, and T cells and B cells were not detected.

Figure 2:
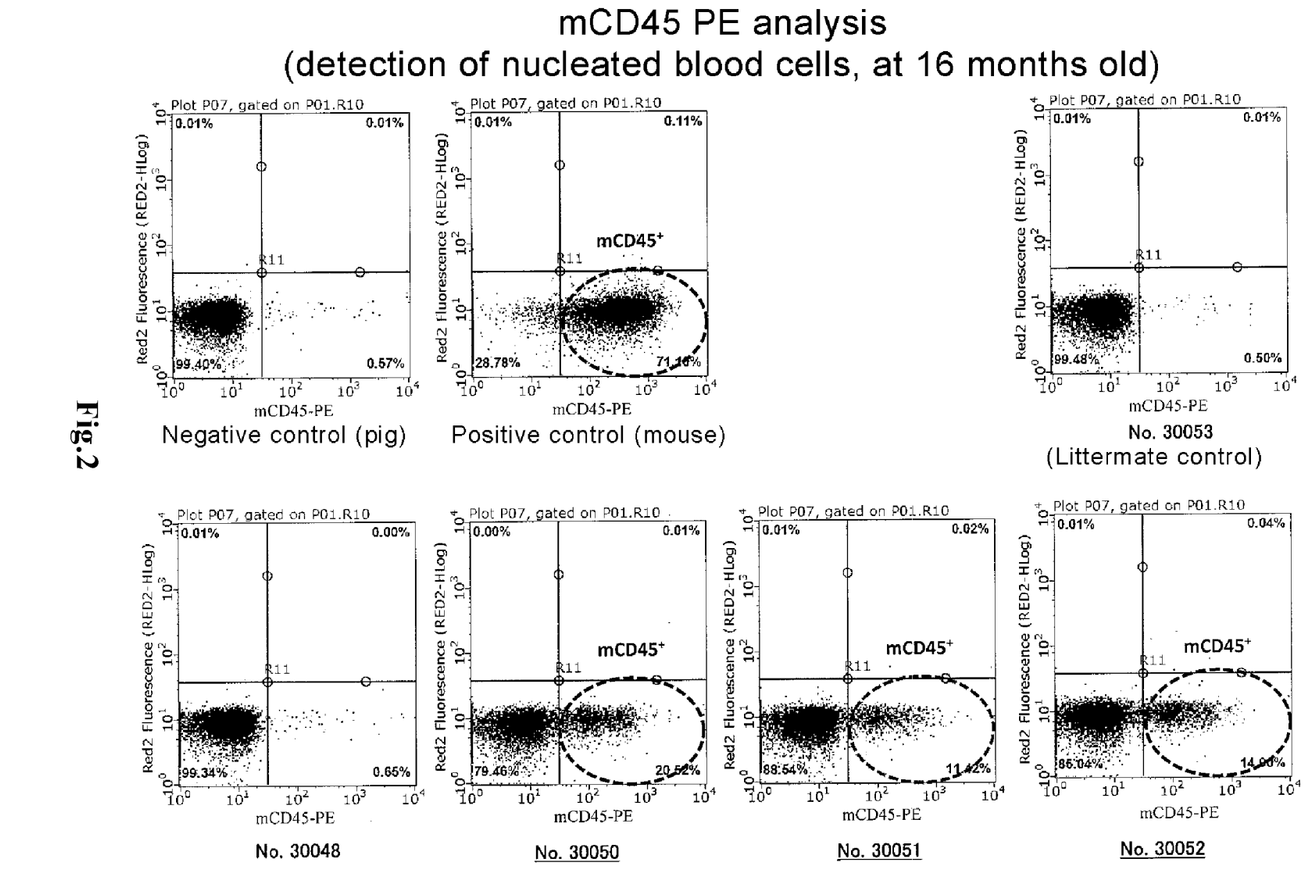
FIG. 2 shows the results of detection of mature murine leukocytes present in the blood of 16 month-old pig offsprings, using a PE-labeled anti-mouse CD45 antibody.
Figure 3:
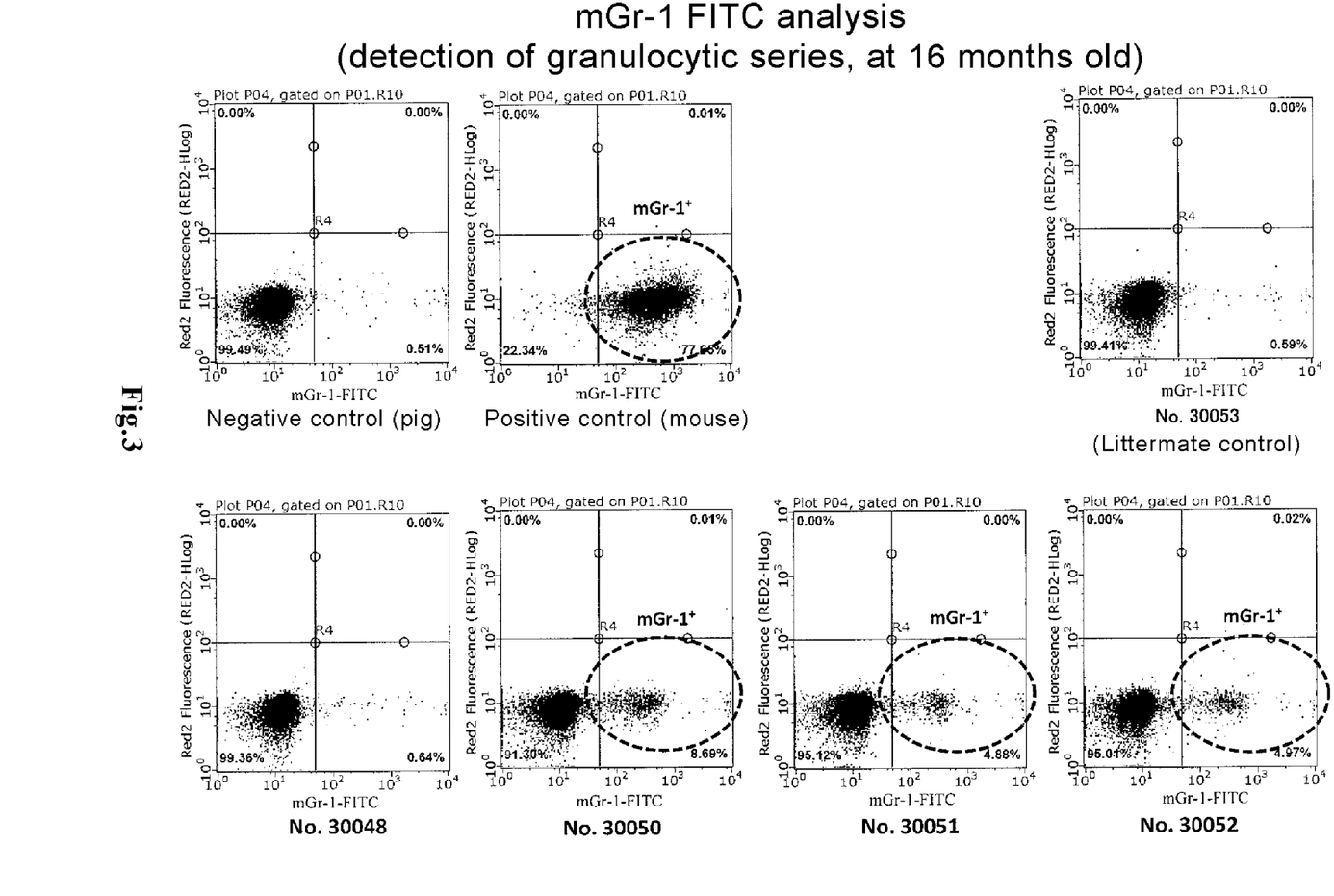
FIG. 3 shows the results of detection of mature murine granulocytes present in the blood of 16 month-old pig offsprings, using a FITC-labeled anti-mouse Gr-1 antibody.
Figure 4:
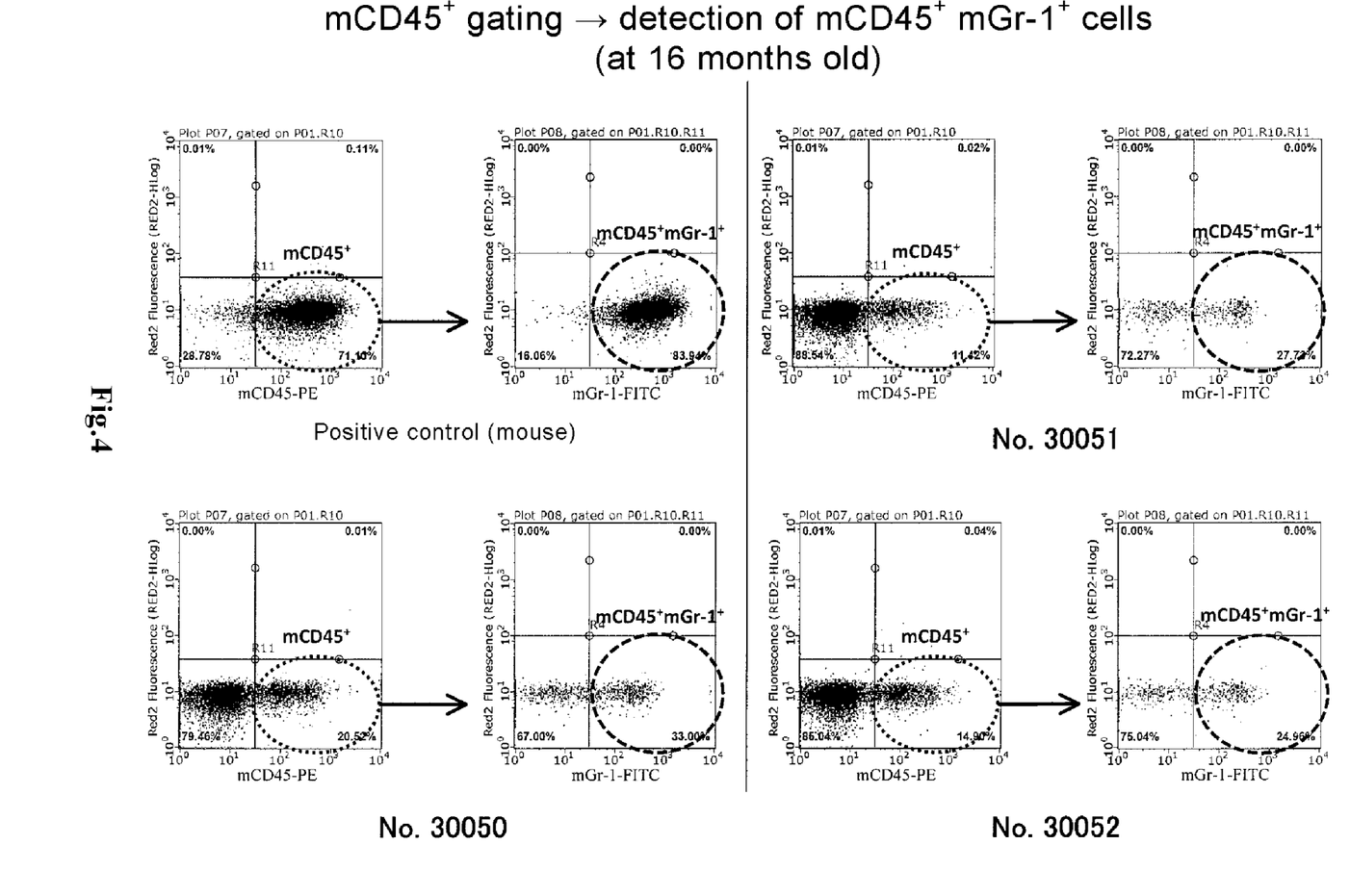
FIG. 4 shows the results of measurement of the percentage of granulocytes in murine leukocytes in the blood samples of 16 month-old pig offsprings, by gating on mouse CD45 positive cells.

FIG. 2 to FIG. 4 show the analysis results of the blood samples from the obtained pig offsprings at 16 months old. It was confirmed that a high level of chimerism was sustained in the cell-transplanted offsprings, even at 16 months old. Each of the analysis results is described hereinbelow.

FIG. 2 shows the results of the detection of mature murine leukocytes present in the blood of 16-month-old pig offsprings using an anti-mouse CD45 antibody. The surface antigen CD45 is expressed on all the nucleated blood cells, and the nucleated blood cells in the peripheral blood (circulating blood) are primarily leukocytes. In each of the three individuals 30050, 30051 and 30052, murine blood cells accounted for 10% or more of the total nucleated blood cells in the circulating blood, showing that a high level of chimerism was sustained. The individual showing the highest chimerism retained the murine nucleated blood cells at an amount of over 20% of the total nucleated blood cells.

FIG. 3 shows the results of the detection of mature murine granulocytes present in the blood of 16 month-old pig offsprings using an anti-mouse Gr-1 antibody. In the three individuals confirmed to be highly chimeric, murine granulocytes accounted for about several percent of all the granulocytes (neutrophils, eosinophils and basophils) in the circulating blood. In a common wild type pig, the percentage of each type of granulocytes in the blood cells is said to be as follows: neutrophils account for 4.4 to 62.1%, eosinophils account for 0 to 11%, and basophils account for 0 to 3.6%.

FIG. 4 shows the percentage of granulocytes in the murine leukocytes measured by gating on mouse CD45 positive cells. In the three individuals confirmed to be highly chimeric, granulocytes accounted for about 25 to 33% of the murine nucleated blood cells.

In the individual 30048, the level of blood chimerism was markedly decreased at the age of 16 months old. The reason for this is thought to be as follows: the transplanted murine hematopoietic stem cells had successfully survived in the bone marrow once, but failed to survive stably thereafter.

On the other hand, the individual 30051 showed an extremely low level of chimerism at 45 days old, but showed a markedly increased chimerism of nucleated blood cells at the age of 16 months old. The percentage of hematopoietic stem cells in the blood cells present in the circulating blood is known to be very low. Thus, in this individual, it is probable that, while murine hematopoietic stem cells survived in the bone marrow at 45 days old, the amount of blood cells differentiated therefrom was too low to be reflected in the level of chimerism of nucleated blood cells in the peripheral blood.

The above-described study demonstrates that pigs which stably retain murine blood cells at a high percentage can be produced by transplanting murine hematopoietic stem cells in which Lnk is knocked out into pigs. The differences in genetic background between humans and pigs, as well as between humans and non-human primates, are smaller as compared to those between mice and pigs; and there are more similarities in the anatomical and physiological characteristics between humans and pigs, as well as between humans and non-human primates, compared to those between mice and pigs. Therefore, when human hematopoietic cells in which the function of the Lnk gene is inhibited are transplanted into a pig or a non-human primate, it is thought to be able to achieve a high survival rate of the human hematopoietic cells, which is comparable to or higher than the survival rate of the murine hematopoietic cells.

The invention claimed is:

1. A non-human animal that retains blood cells originating in a heterologous animal, in which the hematopoietic cells originating in the heterologous animal survive, said hematopoietic cells being cells in which a function of Lnk gene is inhibited, and which retains the blood cells originating in the heterologous animal in the circulating blood and has a chimerism of nucleated blood cells of 10% or more at the age of 3 months old or at a time point 3 months after the transplantation of the hematopoietic cells, wherein the heterologous animal is of a species different from the non-human animal, wherein said non-human animal is a pig, and wherein the heterologous animal is a mammal.

2. The non-human animal according to claim 1, wherein the hematopoietic cells comprise hematopoietic stem cells.

3. The non-human animal according to claim 1, wherein said chimerism of nucleated blood cells is 12% or more.

4. The non-human animal according to claim 1, wherein said chimerism of nucleated blood cells is 15% or more.

5. A method for producing blood cells, the method comprising collecting blood from the non-human animal according to claim 1, and separating the blood cells originating in the heterologous animal.

* * * * *

SEQUENCE LISTING

```
<160> NUMBER OF SEQ ID NOS: 4

<210> SEQ ID NO 1
<211> LENGTH: 5425
<212> TYPE: DNA
<213> ORGANISM: Homo sapiens
<220> FEATURE:
<221> NAME/KEY: CDS
<222> LOCATION: (358)..(2085)

<400> SEQUENCE: 1
cccgggccac cgcctccgcc cggctgcccg cccggactgt cgcggcccgc ggtggcgacg      60
gcggccgctg caaagtttcc ccggcggcgg cggcccgggg gcgcatcctc ccgcaactgt     120
caagcgctgg cggcggaaat gatgaggcgc tggccatttt ccgagcccgg gtttcctgcc     180 tgagcccgc tcgagcgagc cgcgagcgag gagccggcgg gcgggagagg acgcgcccag     240
ggcgggggcc cgcccgcccc ctcgggattt cgagggcccg ggggcgcgcg acgccatggg     300
ccggccgggc ccagagctcc tgtctctcag cccggccgca ccacctgggt ctccgcc        357 atg aac ggg cct gcc ctg cag ccc tcc tcg ccc tct tcc gcg ccc tca      405
Met Asn Gly Pro Ala Leu Gln Pro Ser Ser Pro Ser Ser Ala Pro Ser
1               5                   10                  15 gcc tcc ccg gcg gcg gcc ccg cgg ggc tgg agc gag ttc tgt gag ttg      453
Ala Ser Pro Ala Ala Ala Pro Arg Gly Trp Ser Glu Phe Cys Glu Leu
            20                  25                  30 cac gcc gta gcg gcg gcc cgg gag ctg gcc cgc cag tac tgg ctg ttc      501
His Ala Val Ala Ala Ala Arg Glu Leu Ala Arg Gln Tyr Trp Leu Phe
        35                  40                  45 gcc cgg gag cat ccg cag cac gcg ccg ctg cgc gcc gag ctg gtg tcg      549
Ala Arg Glu His Pro Gln His Ala Pro Leu Arg Ala Glu Leu Val Ser
    50                  55                  60 ctg cag ttc acc gac ctc ttc cag cgc tac ttc tgc cgc gag gtg cgc      597
Leu Gln Phe Thr Asp Leu Phe Gln Arg Tyr Phe Cys Arg Glu Val Arg
65                  70                  75                  80 gac gga cgg gcg ccg ggc cgc gac tac cgg gac aca ggc cgt ggg ccc      645
Asp Gly Arg Ala Pro Gly Arg Asp Tyr Arg Asp Thr Gly Arg Gly Pro
                85                  90                  95
```

```
cca gcc aag gcc gag gcg tcc ccg gag cca ggc ccc ggc ccc gcc gcc        693
Pro Ala Lys Ala Glu Ala Ser Pro Glu Pro Gly Pro Gly Pro Ala Ala
            100                 105                 110 cct ggc ctg ccc aag gcc cgc agc tct gag gag ctg gcc ccg ccg cgg        741
Pro Gly Leu Pro Lys Ala Arg Ser Ser Glu Glu Leu Ala Pro Pro Arg
            115                 120                 125 ccg ccc ggg ccc tgc tcc ttc cag cac ttt cgc cgc agc ctc cgc cac        789
Pro Pro Gly Pro Cys Ser Phe Gln His Phe Arg Arg Ser Leu Arg His
130                 135                 140 atc ttc cgc cgc cgc tcg gcc ggg gag ctg cca gcg gcc cac acc gct        837
Ile Phe Arg Arg Arg Ser Ala Gly Glu Leu Pro Ala Ala His Thr Ala
145                 150                 155                 160 gcc gcc ccc ggg acc ccc gga gag gct gct gag acc ccc gcc cgg cct        885
Ala Ala Pro Gly Thr Pro Gly Glu Ala Ala Glu Thr Pro Ala Arg Pro
                165                 170                 175 ggc ctg gcc aag aag ttc ctg ccc tgg agc ctg gcc cgg gag ccg cca        933
Gly Leu Ala Lys Lys Phe Leu Pro Trp Ser Leu Ala Arg Glu Pro Pro
            180                 185                 190 ccc gag gcg ctg aag gag gcg gtg ctg cgc tac agc ctg gcc gac gag        981
Pro Glu Ala Leu Lys Glu Ala Val Leu Arg Tyr Ser Leu Ala Asp Glu
            195                 200                 205 gcc tcc atg gac agc ggg gca cgc tgg cag cgc ggg agg ctg gcg ctg       1029
Ala Ser Met Asp Ser Gly Ala Arg Trp Gln Arg Gly Arg Leu Ala Leu
210                 215                 220 cgc cgg gcc ccg ggc ccc gat ggc ccc gac cgc gtg ctg gag ctc ttc       1077
Arg Arg Ala Pro Gly Pro Asp Gly Pro Asp Arg Val Leu Glu Leu Phe
225                 230                 235                 240 gac cca ccc aag agt tca agg ccc aag cta caa gca gct tgc tcc agc       1125
Asp Pro Pro Lys Ser Ser Arg Pro Lys Leu Gln Ala Ala Cys Ser Ser
                245                 250                 255 atc cag gag gtc cgg tgg tgc aca cgg ctt gag atg cct gac aac ctt       1173
Ile Gln Glu Val Arg Trp Cys Thr Arg Leu Glu Met Pro Asp Asn Leu
            260                 265                 270 tac acc ttt gtg ctg aag gtg aag gac cgg aca gac atc atc ttt gag       1221
Tyr Thr Phe Val Leu Lys Val Lys Asp Arg Thr Asp Ile Ile Phe Glu
            275                 280                 285 gtg gga gac gag cag cag ctg aat tca tgg atg gct gag ctc tcg gag       1269
Val Gly Asp Glu Gln Gln Leu Asn Ser Trp Met Ala Glu Leu Ser Glu
290                 295                 300 tgc aca ggc cga ggg ctg gag agc aca gaa gca gag atg cat att ccc       1317
Cys Thr Gly Arg Gly Leu Glu Ser Thr Glu Ala Glu Met His Ile Pro
305                 310                 315                 320 tca gcc cta gag cct agc acg tcc agc tcc cca agg ggc agc aca gat       1365
Ser Ala Leu Glu Pro Ser Thr Ser Ser Ser Pro Arg Gly Ser Thr Asp
                325                 330                 335 tcc ctt aac caa ggt gct tct cct ggg ggc ctg ctg gac ccg gcc tgc       1413
Ser Leu Asn Gln Gly Ala Ser Pro Gly Gly Leu Leu Asp Pro Ala Cys
            340                 345                 350 cag aag acg gac cat ttc ctg tcc tgc tac ccc tgg ttc cac ggc ccc       1461
Gln Lys Thr Asp His Phe Leu Ser Cys Tyr Pro Trp Phe His Gly Pro
            355                 360                 365 atc tcc aga gtg aaa gca gct cag ctg gtt cag ctg cag ggc cct gat       1509
Ile Ser Arg Val Lys Ala Ala Gln Leu Val Gln Leu Gln Gly Pro Asp
370                 375                 380 gct cat gga gtg ttc ctg gtg cgg cag agc gag acg cgg cgt ggg gaa       1557
Ala His Gly Val Phe Leu Val Arg Gln Ser Glu Thr Arg Arg Gly Glu
385                 390                 395                 400 tac gtg ctc act ttc aac ttt cag ggg ata gcc aag cac ctg cgc ctg       1605
Tyr Val Leu Thr Phe Asn Phe Gln Gly Ile Ala Lys His Leu Arg Leu
```

|  |  |  |  |  |  |  |  |  |  |  |  |  |  |  |  |
|---|---|---|---|---|---|---|---|---|---|---|---|---|---|---|---|
|  |  |  |  | 405 |  |  |  | 410 |  |  |  | 415 |  |  |  |
| tcg | ctg | aca | gag | cgg | ggc | cag | tgc | cgt | gtg | cag | cac | ctc | cac | ttt | ccc | 1653 |
| Ser | Leu | Thr | Glu | Arg | Gly | Gln | Cys | Arg | Val | Gln | His | Leu | His | Phe | Pro |
|  |  |  | 420 |  |  |  |  | 425 |  |  |  |  | 430 |  |  |

```
                        405                 410                 415
tcg ctg aca gag cgg ggc cag tgc cgt gtg cag cac ctc cac ttt ccc     1653
Ser Leu Thr Glu Arg Gly Gln Cys Arg Val Gln His Leu His Phe Pro
            420                 425                 430 tcg gtc gtg gac atg ctc cac cac ttc cag cgc tcg ccc atc cca ctc     1701
Ser Val Val Asp Met Leu His His Phe Gln Arg Ser Pro Ile Pro Leu
            435                 440                 445 gag tgc ggc gcc gcc tgt gat gtc cgg ctc tcc agc tac gtg gta gtc     1749
Glu Cys Gly Ala Ala Cys Asp Val Arg Leu Ser Ser Tyr Val Val Val
    450                 455                 460 gtc tcc caa cca cca ggt tcc tgc aac acg gtc ctc ttc cct ttc tcc     1797
Val Ser Gln Pro Pro Gly Ser Cys Asn Thr Val Leu Phe Pro Phe Ser
465                 470                 475                 480 ctt cct cac tgg gat tca gag tcc ctt cct cac tgg ggt tca gag ttg     1845
Leu Pro His Trp Asp Ser Glu Ser Leu Pro His Trp Gly Ser Glu Leu
                485                 490                 495 ggc ctt ccc cac ctt agt tct tct ggc tgt ccc cgg ggg ctc agc cca     1893
Gly Leu Pro His Leu Ser Ser Ser Gly Cys Pro Arg Gly Leu Ser Pro
            500                 505                 510 gag ggt ctc cca ggg cga tcc tca ccc ccc gag cag atc ttc cac ctg     1941
Glu Gly Leu Pro Gly Arg Ser Ser Pro Pro Glu Gln Ile Phe His Leu
    515                 520                 525 gtg cct tcg ccc gaa gaa ctg gcc aac agc ctg cag cac ctg gag cat     1989
Val Pro Ser Pro Glu Glu Leu Ala Asn Ser Leu Gln His Leu Glu His
530                 535                 540 gag cct gtg aat cga gcc cgg gac tcg gac tac gaa atg gac tca tcc     2037
Glu Pro Val Asn Arg Ala Arg Asp Ser Asp Tyr Glu Met Asp Ser Ser
545                 550                 555                 560 tcc cgg agc cac ctg cgg gcc ata gac aat cag tac aca cct ctc tga    2085
Ser Arg Ser His Leu Arg Ala Ile Asp Asn Gln Tyr Thr Pro Leu
                565                 570                 575 ccagtgagga attccaggcc tcaacagctg cccttgagga gcacaggcag aagtgtgaac   2145
ttgtgaatgt aattgatctt ccttccttc cagagaaaga tttaagggac actgttaact    2205
gctcgtgcca gtttggaagt gacccttcta ttaggcctgt tgaagggccc tcctgtaggt   2265
ttcatctatc cacctggctt tctccttatt gtttacagat gtagttcttg ttagaggatg   2325
ccgctagctc ctgcccgggg tccctatgcc cagtccccgt tactcttaga gaaaggagtt   2385
ggggtgaggg ccagagctgg cagtggaaac ttgttctctt tttcactgac actgtcacag   2445
cggatgacag actttctacg gggaggaggg ggggatcatc aggaagccca gaacactaac   2505
aagcggttct cccatctacc gtcagtccac atggcaggtc tgctgtgtcc acaccacaga   2565
tgaccacatc taatcctgct tctactctca gctttaggac aaaagctctg tcagaggcac   2625
aagctgaagg tcaaaaatga tttaaaacat tttacctcag actaatttct ttaaaggatt   2685
caggttcaaa acttaaccac tgcttatttc agtgcactgt ttcaactaac acccatgcta   2745
ttttgtagt cagaaacagc tatgcaaacc ctacctaatt tacagtctga gccagcatgc     2805
tggcttgtct actgcatcct cgggacagtc acctgccact gagtggccac tgtccttcct   2865
aaatgtcaag aagtgaagta tgtcaccctt tcagggaaat tcaggcaatt actgaaatag   2925
gagggtggca agaacagttc tatcctggtg ccttacgaat aaaaaactgg attctggttt   2985
acagcagctt tacagtgata gttaaattaa ctggggctag gggaagagca agcaaaaagg   3045
gaagaaggac tcctaggccc tttctagtaa atccttcagc aacaaggctg gcttggtgcc   3105
ctccaagcat ctaatggctt attaaattat cccacaagtg ggttttaggc tcctttttg    3165
agccaaaatg gaagctggga atctggtgcc ataactaatg agaaactcct ttaatagccc   3225
```

```
acaatcagtg ttctgttcta gctggctact gcttcactgg attgagaatc tatctatctc   3285
cttgcacaca tgggcacaca caatctccac catccaggga ggtcctgaag tcaaatctct   3345
atctatacaa gtgatacaat tcataggggg ctggctcctc ccagaacctg tctggaggct   3405
cagaaacggg ggcagtgaca gtggagtcag ctgctcttgg gtgccagcag agccattcag   3465
tacaaccccc aggctcacag cagtggcttc taggaaactg ggagtttaga tcagctttac   3525
agatacatcg atcagaggct aaaatgaaac ctcagcctaa aactcatagg actgactgcc   3585
tgggaggagg gttaggtctg cttcttccac ttatacttag tctctgtgct ccaagaggtc   3645
aaattttgc ttctagaatt tccttggggt ctttcagagg gtggggaac aaaccccctat    3705
gcacttttct tttttttttt tttgagatgg agtttctctt gtcaaccggg ctggagtgca   3765
gtggtgcaat cttggctcac tgcaacctcc accttcctgg ttcaagcgat tctgcctcga   3825
cctctcaagt agctgggatt acaagcacca gccaccatgc ctggctaatt ttgtattttt   3885
agtagagaca gggtttcacc atgttggcca ggctggtctc gaatgtctga cctcaggtga   3945
tccacccgcc ttggcctccc aaagtgctgg gattacaggc gcgagccacc gcgcccagcc   4005
tacaccactt ttagtaccaa cactcttggg tgatttcatg gaccctaaag cagacctgac   4065
actgatccag atttgcagtc cattttaag gacacctgtc tttatttcct caaagtcaag    4125
cagctttctc tggaaaatga atgctaatta gtgtgaacca aaagagtaag taagagtctg   4185
aagtttttt aaaggagaaa gcttattatg gaaagtcact ggtcctcccc tccgcacagg    4245
aaaggtaccc agtagataat gaaccaaatt aagttccctc cctccagcca gaagttaaac   4305
atctgggata tgacgtcttc atgccagggg cactcatttc ttagcagcct ctctacatac   4365
atctctcagg tggtgccaag aggcacacca ggtagagcaa acttagcagc tctgactaac   4425
aggctgcaaa gtgcaagttc agattctgtg gcagagattt ggaaggcacc cacctccaga   4485
ctgcttcccg tccaagttac caggacagct caaaaacatg ctgacagaaa actcccatgg   4545
ctctaggaag aagtgacact aagccaacac cttttctttat gtgggagcag aatcagctga   4605
tgaaggggtg ggcagcagtg tggggcaggc accccactgg ctgcagctag cccaccatag   4665
gcacagcaca tcccaccact ctccttccag tcctgaccag gccccagccg gcaacttcta   4725
ccgagagcca tggctcaaca ccaaactgga cagtagacat catgatccct ccagttagct   4785
ctaattacag accccaccag tacagcttga cagctcccgg caccatccct ccttcatct    4845
gacttattga acttttacaa actaacagtc accagcacca aagaattaag tcaactaacc   4905
tgccttgaat tttagaccag caatccatat ggctttatct ggtataaatc ttctgccttt   4965
gatcatttct ggaccgtagg aaaaaggaat agcaatcatt aaaatcttgg gccagagaac   5025
actatttta cataacagtt tcttaaccta agtcaaggc cttggactct cctgaggg       5085
ttgcctgaga ttccttcatg ctttctattc aggactaagt cccttactgc aaatgtgtta   5145
gctctaacat ctcccacaag ctagaggaac ttgcgagtat attaacaagg acacatctga   5205
catcctgtgt ttggttagaa tatacagcac attgtgataa cataaagtgg attcatcttg   5265
tatcattata ggcagaaggt atttggcaaa ttttatgta ttgttttatg tactgtacaa    5325
gtaacttatt cttgaataat gcaaattttg ctataatgta caaattgcta tatgtgaatt   5385
aaaaagtttt cagaatcttg aaaaaaaaaa aaaaaaaaa                          5425
```

<210> SEQ ID NO 2
<211> LENGTH: 575
<212> TYPE: PRT

<213> ORGANISM: Homo sapiens

<400> SEQUENCE: 2

```
Met Asn Gly Pro Ala Leu Gln Pro Ser Ser Pro Ser Ser Ala Pro Ser
1               5                   10                  15

Ala Ser Pro Ala Ala Pro Arg Gly Trp Ser Glu Phe Cys Glu Leu
            20                  25                  30

His Ala Val Ala Ala Ala Arg Glu Leu Ala Arg Gln Tyr Trp Leu Phe
                35                  40                  45

Ala Arg Glu His Pro Gln His Ala Pro Leu Arg Ala Glu Leu Val Ser
            50                  55                  60

Leu Gln Phe Thr Asp Leu Phe Gln Arg Tyr Phe Cys Arg Glu Val Arg
65                  70                  75                  80

Asp Gly Arg Ala Pro Gly Arg Asp Tyr Arg Asp Thr Gly Arg Gly Pro
                85                  90                  95

Pro Ala Lys Ala Glu Ala Ser Pro Glu Pro Gly Pro Gly Pro Ala Ala
            100                 105                 110

Pro Gly Leu Pro Lys Ala Arg Ser Ser Glu Glu Leu Ala Pro Pro Arg
            115                 120                 125

Pro Pro Gly Pro Cys Ser Phe Gln His Phe Arg Arg Ser Leu Arg His
            130                 135                 140

Ile Phe Arg Arg Arg Ser Ala Gly Leu Pro Ala Ala His Thr Ala
145                 150                 155                 160

Ala Ala Pro Gly Thr Pro Gly Glu Ala Ala Glu Thr Pro Ala Arg Pro
                165                 170                 175

Gly Leu Ala Lys Lys Phe Leu Pro Trp Ser Leu Ala Arg Glu Pro Pro
            180                 185                 190

Pro Glu Ala Leu Lys Glu Ala Val Leu Arg Tyr Ser Leu Ala Asp Glu
            195                 200                 205

Ala Ser Met Asp Ser Gly Ala Arg Trp Gln Arg Gly Arg Leu Ala Leu
            210                 215                 220

Arg Arg Ala Pro Gly Pro Asp Gly Pro Asp Arg Val Leu Glu Leu Phe
225                 230                 235                 240

Asp Pro Pro Lys Ser Ser Arg Pro Lys Leu Gln Ala Ala Cys Ser Ser
                245                 250                 255

Ile Gln Glu Val Arg Trp Cys Thr Arg Leu Glu Met Pro Asp Asn Leu
            260                 265                 270

Tyr Thr Phe Val Leu Lys Val Lys Asp Arg Thr Asp Ile Ile Phe Glu
            275                 280                 285

Val Gly Asp Glu Gln Gln Leu Asn Ser Trp Met Ala Glu Leu Ser Glu
            290                 295                 300

Cys Thr Gly Arg Gly Leu Glu Ser Thr Glu Ala Glu Met His Ile Pro
305                 310                 315                 320

Ser Ala Leu Glu Pro Ser Thr Ser Ser Pro Arg Gly Ser Thr Asp
            325                 330                 335

Ser Leu Asn Gln Gly Ala Ser Pro Gly Gly Leu Leu Asp Pro Ala Cys
            340                 345                 350

Gln Lys Thr Asp His Phe Leu Ser Cys Tyr Pro Trp Phe His Gly Pro
            355                 360                 365

Ile Ser Arg Val Lys Ala Ala Gln Leu Val Gln Leu Gln Gly Pro Asp
            370                 375                 380

Ala His Gly Val Phe Leu Val Arg Gln Ser Glu Thr Arg Arg Gly Glu
385                 390                 395                 400
```

```
Tyr Val Leu Thr Phe Asn Phe Gln Gly Ile Ala Lys His Leu Arg Leu
            405                 410                 415

Ser Leu Thr Glu Arg Gly Gln Cys Arg Val Gln His Leu His Phe Pro
        420                 425                 430

Ser Val Val Asp Met Leu His His Phe Gln Arg Ser Pro Ile Pro Leu
            435                 440                 445

Glu Cys Gly Ala Ala Cys Asp Val Arg Leu Ser Ser Tyr Val Val Val
        450                 455                 460

Val Ser Gln Pro Pro Gly Ser Cys Asn Thr Val Leu Phe Pro Phe Ser
465                 470                 475                 480

Leu Pro His Trp Asp Ser Glu Ser Leu Pro His Trp Gly Ser Glu Leu
            485                 490                 495

Gly Leu Pro His Leu Ser Ser Ser Gly Cys Pro Arg Gly Leu Ser Pro
            500                 505                 510

Glu Gly Leu Pro Gly Arg Ser Ser Pro Glu Gln Ile Phe His Leu
        515                 520                 525

Val Pro Ser Pro Glu Glu Leu Ala Asn Ser Leu Gln His Leu Glu His
            530                 535                 540

Glu Pro Val Asn Arg Ala Arg Asp Ser Asp Tyr Glu Met Asp Ser Ser
545                 550                 555                 560

Ser Arg Ser His Leu Arg Ala Ile Asp Asn Gln Tyr Thr Pro Leu
            565                 570                 575

<210> SEQ ID NO 3
<211> LENGTH: 58
<212> TYPE: DNA
<213> ORGANISM: Artificial Sequence
<220> FEATURE:
<223> OTHER INFORMATION: shRNA construct sequence targeting human Lnk
      gene

<400> SEQUENCE: 3
ccggcctgac aacctttaca cctttctcga gaaaggtgta aaggttgtca ggttttttg         58

<210> SEQ ID NO 4
<211> LENGTH: 58
<212> TYPE: DNA
<213> ORGANISM: Artificial Sequence
<220> FEATURE:
<223> OTHER INFORMATION: shRNA construct sequence targeting human Lnk
      gene

<400> SEQUENCE: 4
ccgggcctga caacctttac accttctcga gaaggtgtaa aggttgtcag gcttttttg         58
```

UNITED STATES PATENT AND TRADEMARK OFFICE
CERTIFICATE OF CORRECTION

| | |
|---|---|
| PATENT NO. | : 11,432,537 B2 |
| APPLICATION NO. | : 15/739059 |
| DATED | : September 6, 2022 |
| INVENTOR(S) | : Kazuo Fukawa et al. |

It is certified that error appears in the above-identified patent and that said Letters Patent is hereby corrected as shown below:

On the Title Page

Item (73) Please change:
"(73) Assignees: THE UNIVERSITY OF TOKYO, Tokyo (JP); NATIONAL FEDERATION OF AGRICULTURAL COOPERTIVE ASSOCIATIONS, Tokyo (JP)"
To:
-- (73) Assignees: THE UNIVERSITY OF TOKYO, Tokyo (JP); NATIONAL FEDERATION OF AGRICULTURAL COOPERATIVE ASSOCIATIONS, Tokyo (JP) --

Signed and Sealed this
Twenty-seventh Day of June, 2023

Katherine Kelly Vidal
*Director of the United States Patent and Trademark Office*